(12) United States Patent
Mohler

(10) Patent No.: US 6,936,827 B1
(45) Date of Patent: Aug. 30, 2005

(54) DETECTING DEVICE FOR FLUORESCENT-LABELED MATERIAL

(75) Inventor: Jerre Wayne Mohler, Trout Run, PA (US)

(73) Assignee: The United States of America as represented by the Department of the Interior, Washington, DC (US)

(*) Notice: Subject to any disclaimer, the term of this patent is extended or adjusted under 35 U.S.C. 154(b) by 56 days.

(21) Appl. No.: 09/788,475

(22) Filed: Feb. 21, 2001

(51) Int. Cl.$^7$ ............................................. G01N 21/64
(52) U.S. Cl. ............................... 250/458.1; 250/459.1; 250/461.1; 250/461.2
(58) Field of Search .................. 250/458.1, 459.1, 250/461.1, 461.2

(56) References Cited

U.S. PATENT DOCUMENTS

| | | | |
|---|---|---|---|
| 4,056,724 A | 11/1977 | Harte | |
| 4,178,917 A | 12/1979 | Shapiro | |
| 4,198,567 A | 4/1980 | Eneroth et al. | |
| 4,884,890 A * | 12/1989 | Coates | 356/384 |
| 4,905,169 A | 2/1990 | Buican et al. | |
| 5,166,813 A * | 11/1992 | Metz | 359/15 |
| 5,239,998 A | 8/1993 | Krauthamer | |
| 5,324,940 A * | 6/1994 | Eckstrom | 250/302 |
| 5,370,119 A | 12/1994 | Mordon et al. | |
| 5,440,927 A * | 8/1995 | Chu et al. | 73/335.01 |
| 5,628,310 A | 5/1997 | Rao et al. | |
| 5,639,668 A * | 6/1997 | Neel et al. | 436/172 |
| 5,968,479 A | 10/1999 | Ito et al. | |

OTHER PUBLICATIONS

Mohler, J.W., "Immersion of Larval Atlantic Salmon in Calcein Solutions to Iniduce a Non-Lethally Detectable Mark," *North American Journal of Fisheries Management*, 17:751-756 (1997).

* cited by examiner

Primary Examiner—Constantine Hannaher
(74) Attorney, Agent, or Firm—Mark Homer

(57) ABSTRACT

A fluorochrome-marked sample is excited with the proper wattage and wavelength of light using an exciter or bandpass filter and beamsplitting mirror device. This causes the sample to emit light of a slightly higher wavelength than that of excitation. A subsequent barrier filter of the proper configuration placed between the sample and the observer allows this longer wavelength to be observed as fluorescence. This technique is particularly useful for viewing large biological specimens such as fish.

7 Claims, 5 Drawing Sheets

FIGURE 1 Prototype hand-held calcein detection device
(for detection of visible fluorescence emitted from calcein-labeled biological tissues or other material)

FIGURE 2 (Alternative embodiment) Prototype bench-top calcein detection device for detection of visible fluorescence emitted from calcein-labeled biological tissues or other material

# DETECTING DEVICE FOR FLUORESCENT-LABELED MATERIAL

FIELD OF THE INVENTION

The present invention relates to a hand-held or bench-top fluorescence detector for fluorescent labeled material.

BACKGROUND OF THE INVENTION

Fry stocking is a primary management strategy of the U.S. fish and wildlife Service and cooperating state fishery agencies for restoring populations of fish, for example, restoring Atlantic salmon, *Salmo salar*, to the New England states. In order to determine the effectiveness of this strategy in achieving management goals, identification of stocked fish is critical. Therefore, it would be useful to have a technique for marking larval (nonfeeding) fish with a readily recognizable tag or mark capable of being non-lethally detected in fry, parr, smolts, and returning adult fish.

A variety of attempts have been made to mark salmonid fry by mechanical or chemical techniques. Unfortunately, none of these methods has been adequately refined or proven practical for marking large numbers of Atlantic salmon fry with a feature that can be non-lethally detected in subsequent life stages of the fish. Kaill et al. (1990) evaluated the use of half-length coded wire tags in emergent pink salmon *Oncorhynchus gorbuscha* and reported short-term retention rates of 93–100% and long-term retention rate estimates of 50–84%.

This technique was tested on Atlantic salmon larvae in 1994 by U.S. Fish and Wildlife biologists at the Northeast Fishery Center, Lamar, Pa., but proved to be ineffective and impractical with this species due to the small size of fry (J. W. Fletcher, NEFC, personal communication). In general, chemical marks induced in fish from immersion in dyes or stains produce short-term marks that are detectable only for days, rather than for years. Injecting dyes and stains produces more durable marks, but the fish are subjected to greater stresses during handling and marking (Muncy et al., 1990). Immersion, injection, or feeding of fluorescent chemicals, such as oxytetracycline, can produce a mark on calcified fish tissues that is delectable under ultraviolet light or through fluorometric techniques (Muncy et al., 1990). Oxytetracycline has been used to mark teleost otoliths for subsequent age validation, but the fish must be sacrificed for mark determination. Wilson et al. (1987) reported that calcein, a compound that fluoresces green under long wave ultraviolet light, produced a detectable mark on otoliths of three species of estuarine fish afer a two hour immersion in a calcein solution of 125 mg/L.

Calcein chemically binds with calcium and shows a marked increase in fluorescence when complexed with alkaline earth metals (Wallach et al., 1959). Calcein has been used as an indicator to determine the calcium content of limestone and gypsum (Diehl and Ellingboe, 1956), for determining submicrogram quantities of cadmium (Hefley and Jaselskis, 1974), as a stain for angiography (Oncel et al., 1990), and for fitting soft hydrophilic contact lenses (Refojo et al., 1972).

Prior methods for detecting fluorescent-labeled organisms required use of a microscope outfitted with the proper filters for detecting fluorescing marks in fish or other biological materials. This created the problem of transporting an expensive, delicate microscope into outdoor and harsh environments, and required that individual specimens be placed onto the microscope stage for examination. Microscope stages are not intended for examination of whole, live specimens. Even specimens which could be partially examined via microscopy were subject to excessive manipulation and focusing time to attempt evaluation for the fluorescing mark. These procedures are prohibitory for efficiently evaluating large-sized specimens or large numbers of individuals while maintaining the life of live specimens if necessary.

One conventional detector for incident light fluorescence is the AO Vertical Illuminator for Light Fluorescence microscopy, produced by Reichert Scientific Instruments, Buffalo, N.Y., which is based on microscopy. This conventional illuminator module comprises a tungsten halogen lamp or a mercury vapor lamp to provide a source of excitation energy, collector lens system and filed diaphragm to efficiently control the beam, exciter filters to transmit selected wavelengths, dichroic beamsplitters to selectively reflect and subsequently transmit desirable wavelengths, and barrier filters to bar unwanted wavelengths. The dichroic element reflects excitation energy wavelengths up to a predetermined cutoff point. Longer wavelengths, as emitted by fluorescence energy, pass through the dichroic element and are not deflected from their paths. Excitation energy, which is beamed from the lamp through the exciter filter, is reflected by the dichroic element down through the microscope objective into the specimen. Fluorochromes within a specimen, excited by the energy beam from the objective, emit visible fluorescence energy which returns up though the microscope objective, dichroic element, and barrier filters to the microscope eyepiece or camera.

Methods for monitoring using fluorescence include that shown in Rao et al., U.S. Pat. No. 5,628,310. This method is for transdermal measurements of the fluorescence lifetime of an implanted element. This method, however, requires implantation of the fluorescent device.

Krauthamer, in U.S. Pat. No. 5,239,998, discloses a method and apparatus for detecting fluorescence emitted at a remote situs, namely, tissue stained with a voltage-sensitive dye. This method and apparatus are designed to record the electrical activity of tissues stained with voltage-sensitive dyes rather than to detect marked tissues.

Harte, in U.S. Pat. No. 4,056,724, discloses a fluorometric system for detection of sample substances derived from biological fluid, or tissue targeted with fluorochromes. This apparatus requires that the sample substance be coated over a surface on a solid substrate, which means that it cannot be used to detect fluorescence in whole animals.

Thus, there is a need for batch-marking small organisms such as fish and other animals, along with a need for practical, non-lethal field detection of the mark in order to differentiate between groups of organisms, such as hatchery-reared vs wild fish. There is a need for a portable device which can withstand the rigors of outdoor field work and be used to examine samples too large for standard microscopy.

SUMMARY OF THE INVENTION

It is an object of the present invention to overcome the aforesaid deficiencies in the prior art.

It is another object of the present invention to provide a device for determining the presence or absence of a fluorescent marker in calcified biological tissues and other materials after exposure to a fluorochrome.

It is a further object of the present invention to provide a device for use in the field to differentiate between marked and unmarked individuals without the aid of a microscope.

According to the present invention, the proper combination of light, light filters, and other lenses with the known properties of the fluorochrome chemical being detected results in visible detection of the chemical as it fluoresces a characteristic color after it becomes bound to calcified tissues of biological origin.

For purposes of the present invention, any fluorochrome or fluorescing material which can be applied to a biological, natural, or synthetic material which is capable of being labeled such that fluorescence occurs can be detected with the device of the present invention. Filters and lenses in the device can be interchanged with other filters and lenses to detect specific fluorochromes or fluorescing material.

A fluorochrome-marked sample is excited with the proper wattage and wavelength of light using an exciter or bandpass filter. This causes the sample to emit light of a slightly higher wavelength than that of excitation. A subsequent barrier filter of the proper configuration placed between the sample and the observer allows this longer wavelength to be observed as fluorescence. A beamsplitting mirror device may or may not be incorporated to deflect the light path and/or enhance fluorescence detection. This technique is particularly useful for viewing large biological specimens such as fish.

The device of the present invention is particularly useful for samples in which microscopic examination is not practical or desirable, e.g., because of the size of the sample to be examined, the physical nature of the location when detection must occur, or other limitations.

In one embodiment of the invention, a set of eyeglasses made of the same glass used for the longpass barrier filter are worn by the operator to view the specimen from any vantage point as long as light from the detector strikes the specimen. This allows the operator greater freedom of movement and does not restrict the sample size.

DETAILED DESCRIPTION OF THE INVENTION

The present invention permits gross examination of fish or other biological or non-biological material for the presence or absence of a fluorochrome dye, which is manifested as visible fluorescence. The presence of fluorescence from the organism or material being examined is a verification of past marking of the sample.

Apparatus

Figure 1:
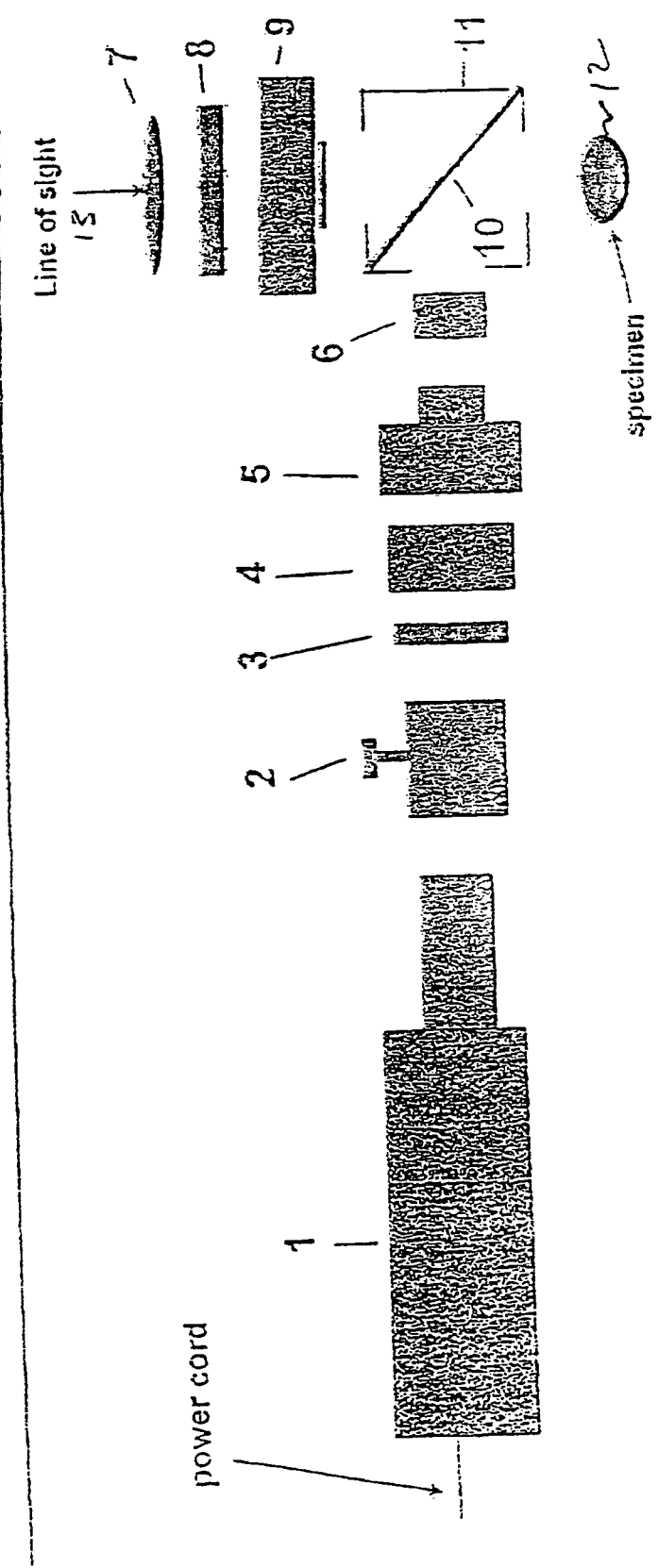
FIG. 1 shows a hand-held fluorescence detection device for detecting visible fluorescence emitted from fluorescent-labeled samples.
Figure 3:
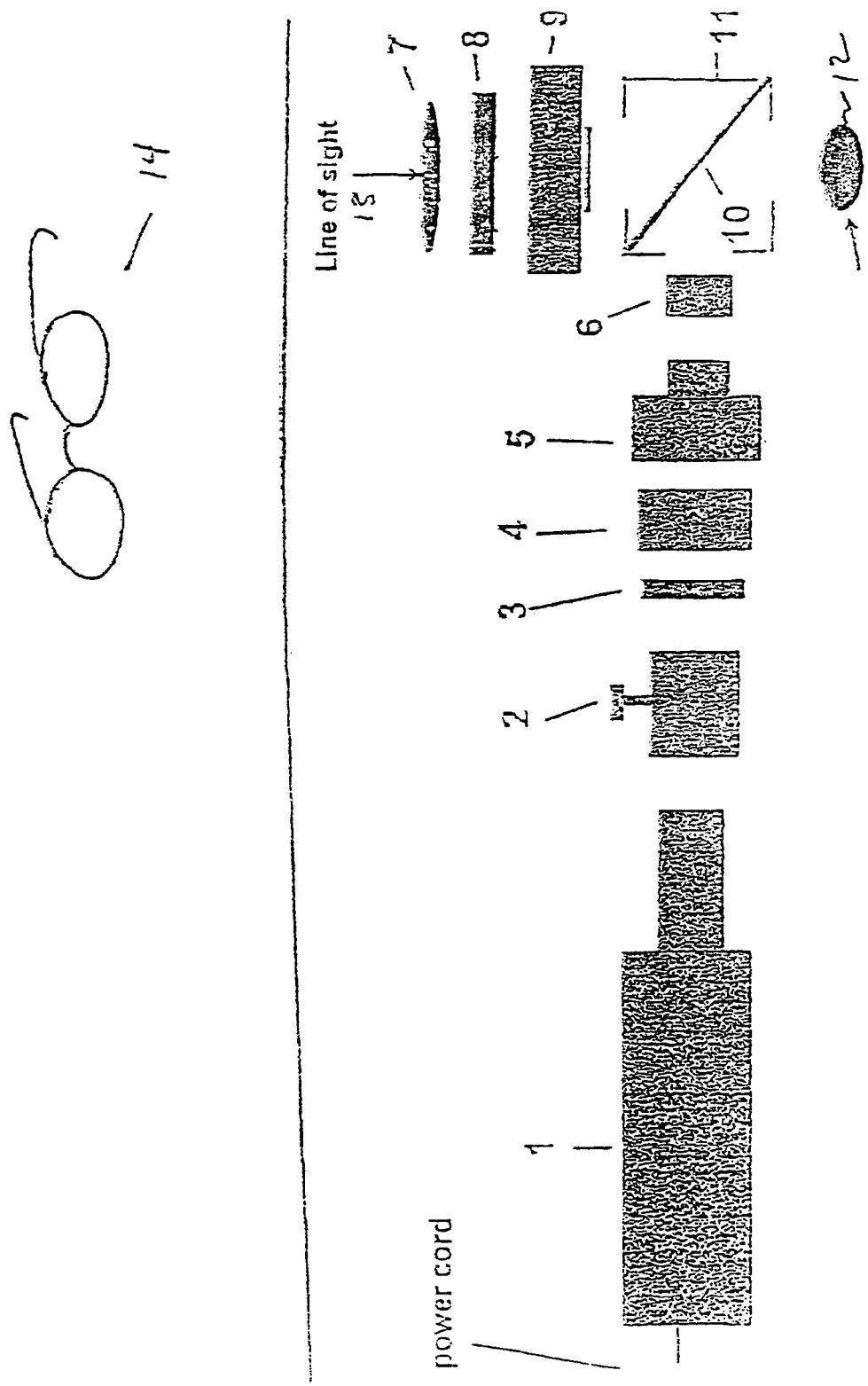
FIG. 3 shows detection of a sample using eyeglasses having the same glass used for the long pass barrier filter.

Referring to FIG. 1, light generated by a hand-held illuminator (AC or battery-powered) 1 passes through an exciter or bandpass filter 3, allowing only a first predetermined wavelength or range of wavelengths of light to pass through. This filter is held in place by a mount 2 and a lens holder 4. The light beam strikes the beamsplitter 10 and is directed down toward a specimen 12, which is excited by the incident light. The beamsplitter 10 is held to the light source by means of adapter 5, and an extension tube 6 provides mechanical clearance. If the specimen contains sufficient fluorochrome, the specimen will emit light of a slightly longer wavelength than that of the incident light. This emitted light will be reflected upwards from the specimen and through the beamsplitter 10 upwardly towards the line of sight. From the beamsplitter, the emitted light will then pass through the barrier or longpass filter 8 where only light greater than a second predetermined wavelength, which is longer than the first predetermined wavelength, will be allowed to pass to the eye of the observer (line of sight 13). Alternatively, as shown in FIG. 3, an operator wearing eyeglasses 14 equipped with the same lenses as in the barrier or long pass filter 8 can view the emitted fluorescence from any vantage point and is not limited by the geometry of the hand-held device. The presence of fluorochrome in the specimen will cause a visible fluorescence to occur. The achromatic lens 7 will provide some magnification of the fluorescing object to the viewer. A barrier filter 8 and achromatic lens 7 are held to the beam splitter by a threaded lens holder 9.

Where the indicator is calcein, the first predetermined wavelength is approximately 490 nm, and the second predetermined wavelength is approximately 520 nm. The emitted fluorescence is green. However, the first and second predetermined wavelengths can be adjusted by substituting specific filters and beamsplitters depending upon the fluorochrome used.

There is no preferred difference between excitation and emission wavelengths. For example, calcein has a range of 500–550 nanometers for emission. The emission wavelength of the fluorochrome used must be sufficiently higher than the excitation wavelength of the fluorochrome.

The greater the amount of light (lumens) striking the sample though the illuminator, the greater the detection sensitivity for fluorescence will be. It has been found that any 100-watt or greater fiber optic light source can be used in the present invention. Wattage is not the ultimate determination of the power of the detector, but what is determinative is how much light (watts, lumens, etc.) of the proper wavelength actually strikes the sample. While light, such as produced by light bulbs, is composed of a wide range of wavelengths, the filters placed into the device allow only those specific wavelengths already present in their respective quantities to pass through.

Any type of light may be used to excite the fluorochrome, including light from a mercury vapor lamp, a tungsten halogen, xenon, laser, or any combination of light sources.

The preferred condition for detecting fluorescence with the device of the present invention is a completely dark environment, so that the fluorescence is most easily visible. However, certain fluorochromes, such as calcein, can be detected under low to moderate lighting as well. Also, as some fluorochromes may not be readily detected in acidic or basic environments, the particular fluorochrome used may be chosen based upon its activity in the particular environment in which it is to be used.

In another embodiment of the present invention, the device rests on a flat surface such as a table or bench top. In addition, a fiber-optic light source can be used rather than a standard illuminator. All of the filters and lenses are similar to the device described above, except that they are all housed in a single structure known as a fluor-cluster, which is positioned at the tip of a flexible fiber optic gooseneck or light guide. This embodiment provides a larger target area for detecting fluorescence, since a higher power light source can be used. This embodiment makes it possible to examine multiple organisms or samples simultaneously, depending upon the size of the sample. Large numbers of samples can be processed more efficiently than would be possible by examining one sample at a time.

Figure 2:
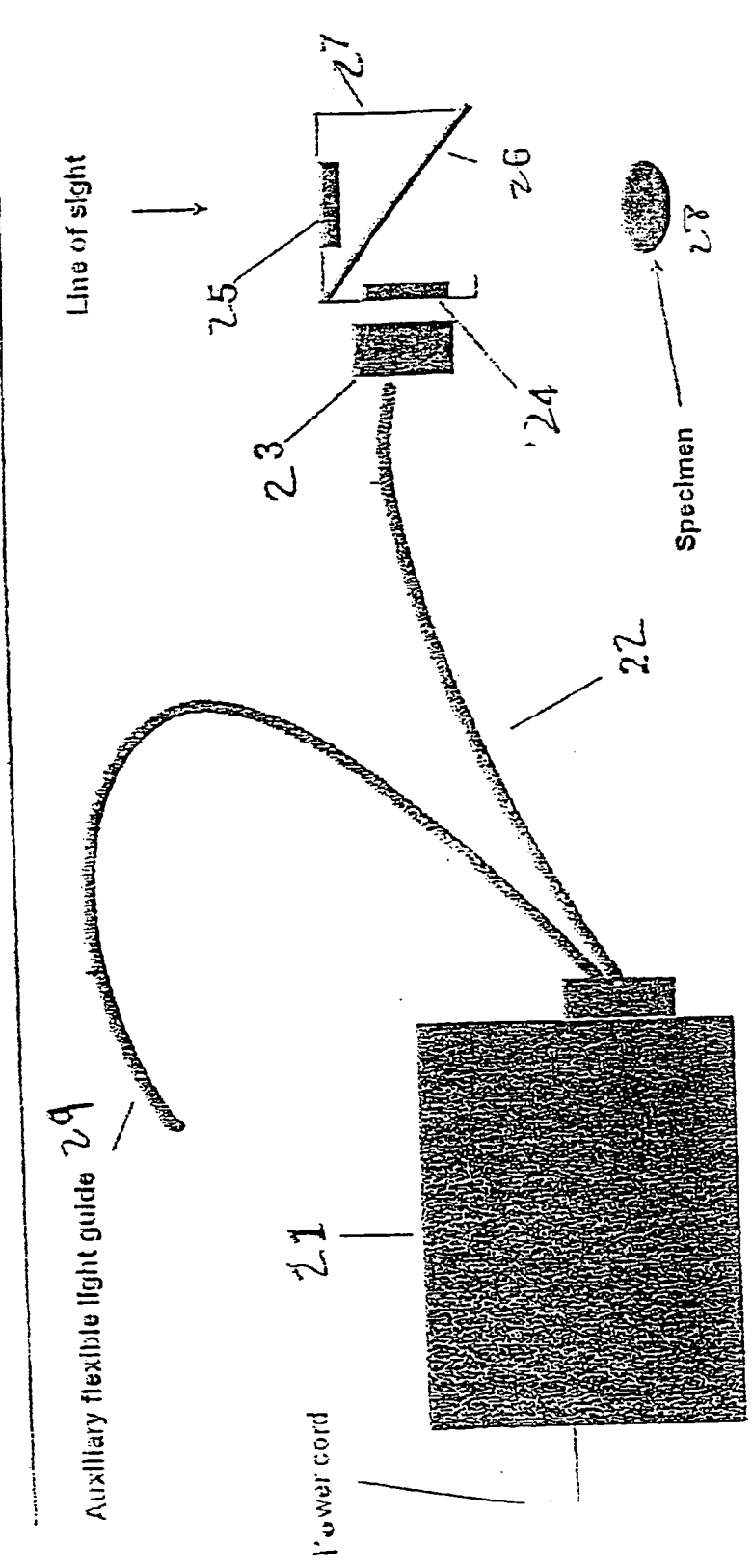
FIG. 2 shows a bench-top fluorescence detection device for detecting visible fluorescence emitted from fluorescent-labeled samples.

This alternative embodiment is shown in FIG. 2. Light generated by a power supply 21 travels through a flexible light guide 22 and is directed through and processed by an exciter or bandpass filter 24. An adapter 23 facilitates attachment of the light guide 22 to a fluor-cluster housing 27. The light hits a beamsplitter 26 and is directed downwards towards the specimen 28. If the specimen contains sufficient fluorochrome, it will emit light of a slightly longer wavelength than that of the incident light. This emitted light will be reflected upwards from the specimen 28 through a beamsplitter 26 and travel towards the line of sight. Emitted light will then pass through a barrier or longpass filter 25, where only light having a wavelength longer than that of the incident light will be allowed to pass to the eye of the observer (line of sight). The presence of a fluorochrome in the specimen will cause a visible fluorescence to occur.

Figure 4:
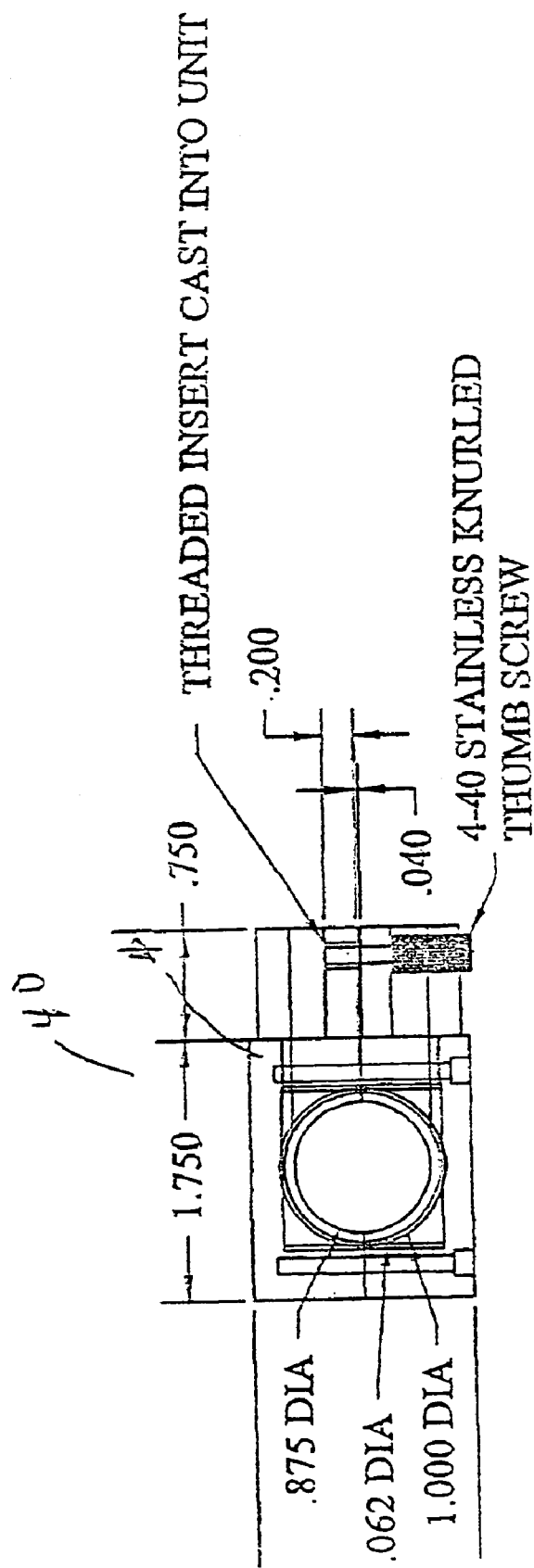
FIG. 4 shows a hand-held calcein detector.

FIG. 4 shows a hand-held fluorochrome detector 40 including fluor-cluster filter housing 41 using a battery-operated light source (not shown). Optional filter glasses can be used so that the operator can view a sample from any vantage point as long as the excitation light is visible.

Figure 5:
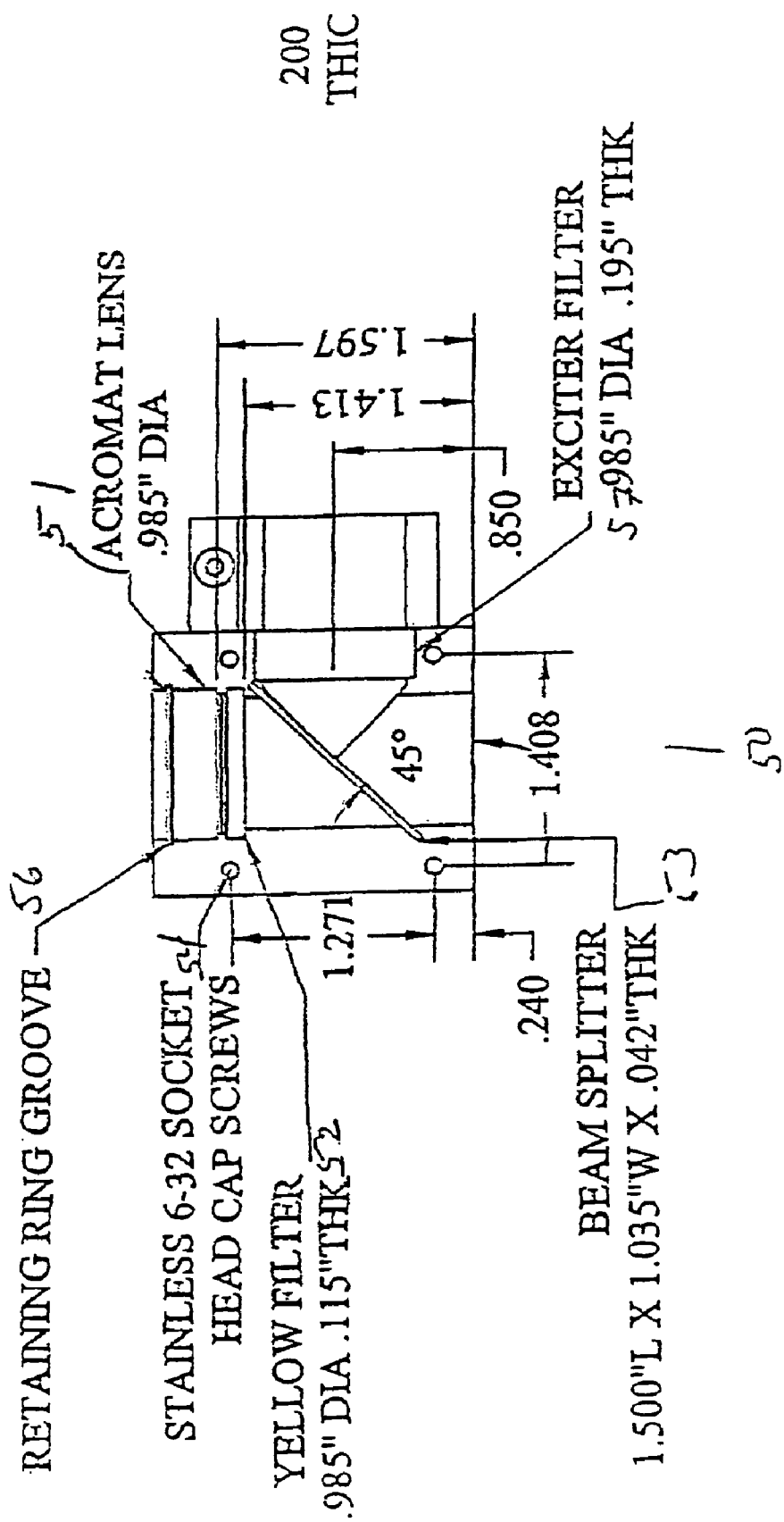
FIG. 5 shows a cutaway view of a fluorochrome detector.

FIG. 5 shows a cutaway view of the filter housing 50 of the fluorochrome detector of the present invention, including an achromatic lens for magnification 51, a longpass barrier filter 52, a coated beamsplitter 53, head cap screws 54 to secure the two halves of the filter housing, a bandpass exciter filter 57, and a retaining ring groove 56.

The filter housing is interchangeable between the bench-top and hand-held fluorochrome detectors.

Principles of Fluorescence Detection

Excitation energy is beamed from a light source through an exciter filter, a filter located between the light source and the sample to screen out undesired wavelengths of light and allow a select band of excitation radiation to pass through to the sample. Selected wavelengths of light energy which pass through an exciter filter are able to cause a sample or specimen which contains material such as a fluorochrome compound, to emit light energy of some greater wavelength value. The emitted light energy then passes through a barrier filter which blocks out unwanted background illumination allowing the observer to detect visible fluorescence.

Also incorporated into the present invention is a dichroic beamsplitter. This is a highly efficient beamsplitter that selectively reflects virtually all of the desirable short wavelength exciting light to the specimen, and selectively transmits the longer wavelength fluorescence emitted from the specimen for detection by the observer. The dichroic beamsplitter reflects excitation energy wavelengths up to a predetermined cutoff point. Longer wavelengths, such as those emitted by fluorescence energy, pass through the beamsplitter and are not deflected from their paths. The beamsplitter enhances but is not critical to the detection of fluorescence. It also serves to redirect all desired wavelengths of light at an angle of 90 degrees from the light source to the line of sight through the detection device to facilitate observation of fluorescence by the observer.

Marking Specimens

While the method and apparatus of the present invention can be used for detecting fluorescence in any type of material, they are particularly useful in detecting fish which have been labeled as fry, or other animals that have been labeled and released to the wild or are subjects of experimental comparison to determine, after a period of time, which of the animals are still extant.

One method for labeling fish fry is by immersion in a solution of a suitable fluorescent material, such as calcein. Fish can be immersed at any age, which for Atlantic salmon can be performed as early as prior to the onset of exogenous feeding, approximately 60 days post-hatch.

In one method of labeling fish fry, solutions of 125 mg/L calcein and 250 mg/L calcein were prepared. Test jars were filled with hatchery water minus 300 mL. Two hundred larvae were placed into each jar, followed by 300 mL of one of the calcein solutions mixed to achieve the desired chemical concentrations. Single-bubble aeration was introduced via 3.2 mm diameter plastic tubing to prevent oxygen depletion during the static, 48 hour immersion. Ambient-temperature water was allowed to flow around the outside of the test jars to keep water temperatures stable. At the end of 48 hours, water quality characteristics (pH, temperature, and dissolved oxygen) were recorded and fresh flow-through water was introduced to all jars, thereby flushing the calcein solutions.

At the onset of exogenous feeding, live brine shrimp *Artemia* sp., supplemented with a formulated dry diet, were introduced equitably into each replicate daily. As reported in Mohler, *North American Journal of Fisheries Management* 17:751–756, 1997, samples were taken from the fins of fish and samples were viewed under fluorescent microscopy.

Gross examination of the fish at ten days postimmersion under fluorescent microscopy revealed that al fish from both calcein treatments has acquired a mark that was detected as apple-green fluorescence in visible bony structures.

After 234 days postimmersion the calcein marks were generally retained at the point of origin. Loss of brilliance at the distal edge of the marked area of the caudal fin suggested that some calcein diffused into developing fin ray tissue during growth. However, if the proper area is located in the sample area of the detection device, detection is reliable. Later, unpublished experiments showed that calcein can be induced into calcified tissues in as little as 7 minutes by immersing fish into hyper-osmotic solutions of saltwater (1–5% salinity) for 3.5 minutes followed immediately by a 3.5 minute bath in a concentrated calcein solution (0.5–1.0%). This technique induced a calcein mark on fin rays and bones of Atlantic salmon with greater consistency and brilliance than previously reported using a passive immersion for 24–48 hours in duration.

The device of the present invention makes it possible to examine much larger samples than was possible with the prior art. Moreover, living macro-organisms, such as fish, can be non-lethally examined. The device of the present invention can be readily transported into harsh environmental conditions for field work, and a large number of samples can be quickly examined. The device of the present invention provides a wider field of view of detection of fluorescence than that of the prior art, and is less expensive the previously used microscopes.

As noted above, any fluorochrome can be used in the present invention as long as the emission wavelength is sufficiently longer than the excitation wavelength to be detected by the device described herein. Of course, for a live sample, the fluorochrome is chosen to be non-toxic. Other considerations for non-live samples include non-reactivity with the sample material.

The following list of fluorochromes is meant to illustrate types of fluorochromes that can be used, including their excitation and emission spectra. However, this list is for purposes of illustration only, and is not meant to be limiting.

| Fluorochrome | Spectral Data | |
|---|---|---|
| | Excitation | Emission |
| Acridin yellow | 470 | 550 |
| Acridin organe + DNA | 502 | 526 |
| Acridin orange + RNA | 460 | 526 |
| Acriflavin-Feulgen | 480 | 550–600 |
| Adrenaline | — | — |
| Alizarin complexon | 530–560 | 580 |
| Allophycocyanin | 630 | 660 |
| AMCA | 345 | 425 |
| 7-Amino-actinomycin D | 555 | 655 |
| Amino-methylcumarine | 354 | 441 |
| 6-Amino-Quinolin | 360 | 443 |
| Atebrin | 436 | 490 |
| Auramin | 460 | 550 |
| Auraphospinmin | 460 | 550 |
| BAO (Ruch) | 280 | 460 |
| BCECF | 430/480 | 520 |
| Berberine sulfate | 430 | 550 |
| BOBO-1 | 462 | 481 |
| BOBO-3 | 570 | 602 |
| BODIPY | 503 | 512 |
| BODIPY 581/591 phalloidin | 584 | 592 |
| Calcein | 495 | 500–550 |
| Calcein blue | 375 | 420–450 |
| Calcium Crimson | 588 | 611 |
| Calcium Green | 506 | 534 |
| Calcium Orange | 554 | 575 |
| Calcofluorwhite | 440 | 500–520 |
| Cascade blue | 376/399 | 423 |
| Catecholamine | 410 | 470 |
| Chinacrin | 450–490 | 515 |
| Chlorotetracycline | — | — |
| Chromomycin/mitramycin | 436–460 | 470 |
| Coriphosphin | 460 | 575 |
| CPM | 385 | 471 |
| CTC 5-cyano-2,3-ditolyl-Tetrazolium-Chlorid | 602 | — |
| Cyanine Cy2 | 489 | 505 |
| Cyanine Cy3 | 575 | 605 |
| Cyanine Cy5 | 640 | 705 |
| Dansylamide | 340 | 578 |
| Dansylchloride | 380 | 475 |
| DAO | — | — |
| DAPI + DNA | 359 | 461 |
| DASPMI | — | — |
| DiBAC4 Dibutylbarbituric acid trimethine oxonol | 439 | 516 |
| DIDS thiocyanato-stilbene | 342 | 418 |
| DilC3/4/12/22 indocarbocyanine | 540–560 | 556–575 |
| DiOC2/7/16 carbocyanine | 550 | 580 |
| DiSC1/2/3/6 thiacarbocyanine | 559 | 585 |
| Diaminonapytylsulfanic acid | 340 | 525 |
| DPH | 350 | 452 |
| Dopamin | 340 | 490–520 |
| DTAF | 495 | 528 |
| Ethidium bromide + DNA | 510 | 595 |
| Euchrysin | 430 | 540 |
| Evans blue | 550 | 611 |
| Fastblue | — | — |
| Feulgen | 480 | 560 |
| FIF-Falk | 405 | 435 |
| Fluo-3 | 480 | 520 |
| FLURAM Fluorescamine | — | — |
| FDA Fluoresceindiacetate | 499 | — |
| FITC Fluorescein-isothiocyanate | 490 | 525 |
| Fluorogold | 350–395 | 530–600 |
| Blue FluoSpheres | 360 | 415 |
| Crimson FluoSpheres | 625 | 645 |
| Red FluoSpheres | 580 | 605 |
| Dark Ref FluoSpheres | 650 | 690 |
| Yello-Green FluoSpheres | 490 | 515 |
| FURA-2 | 340/380 | 500/530 |
| Generic blue/green combination | — | — |
| GFP blue (Green Fluoresc. Protein) | 382 | 448 |
| GFP green | 471 | 503 |
| GFP Mutant W | 458 | 480 |
| GFP Wild Type | 396 | 508 |
| Haematoporphyrin | 530–560 | 580 |
| Hoechst 33258 (Bisbenzmid) | 365 | 480 |
| Hoechst 33342 (Bisbenzimid) | 355 | 465 |
| ImaGene Green substrates | — | — |
| ImaGene Red substrates | — | — |
| Indo-1 | 360 | 410/480 |
| Life/Dead Viability/Cytotoxity Kit | — | — |
| Lissamin-Rodamin B | 535 | 580 |
| Lucifer Yellow | 428 | 540 |
| Magdal red | 540 | 570 |
| Mepacrin | — | — |
| Merocyanine | 555 | 578 |
| MEQ, methoxy-ethylquinoliniuum | 344 | 442 |
| 4-Metylumbelliferon | 360 | 450 |
| Methyl green/pyronin stilbene | — | — |
| Mithramycin | 420 | 575 |
| NBD-Amine | 460–485 | 534–542 |
| NBD - chloride | 480 | 510–545 |
| Nile redt | 485 | 525 |
| Noradrenaline | 340 | 490–520 |
| Olivomycin | 350–480 | 470–630 |
| Oxytetracyclin | — | — |
| Pararosaniline-Feulgen | 560 | 625 |
| PBFI | 340/380 | 420 |
| Phosphine | 465 | 565 |
| C-Phycocyanine | 605 | 645 |
| R-Phycocyanine | — | — |
| B-Phycoerythrine | 546/565 | 575 |
| R-Phycoerythrine | 480–550 | 578 |
| PKH 26 (Sigma) | 551 | 567 |
| POPO-1 | 434 | 456 |
| POPO-3 | 534 | 570 |
| Primulin | 410 | 550 |
| Propidium iodide | 536 | 617 |
| Pyren | 343 | 380–400 |
| Pyrolidin-Methyltetra-cycline | — | — |
| Pyronin | 490–580 | 530–610 |
| QUIN 2 | 340/365 | 490 |
| Quinacrine mustard | 440 | 510 |
| Resorufin | 571 | 585 |
| Rhodamine | 540–560 | 580 |
| Rhodamine 123 | 540–560 | 580 |
| Rhodamin Phalloidin | 550 | 575 |
| Rhodol green | 500 | 525 |
| Acid fuchsine | 540 | 630 |
| SBFI | 340/380 | 420 |
| Serotonin | 365 | 520–540 |
| SNARF | 480 | 600/650 |
| Stilbene SITS, SITA | 365 | 460 |
| Sulfaflavin | 380–470 | 470–580 |
| Tetracycline | 390 | 560 |
| Tetrametylrhodamin | 540 | 566 |
| Texas red | 595 | 620 |
| Thioflavin | 430 | 550 |
| Thiazin red | 510 | 580 |
| TMA-DPH | 355 | 430 |
| TOTO-1 + DNA | 509 | 533 |
| TOTO-3 + DNA | 642 | 661 |
| TRITC | 540 | 580 |
| XRITC | 560 | 620 |

-continued

| Fluorochrome | Spectral Data | |
|---|---|---|
| | Excitation | Emission |
| YOYO-1 | 491 | 509 |
| YOYO-3 | 642 | 660 |
| Xylenol orange | 377 | 610 |
| Immunogold, Silver | — | — |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

REFERENCES

Diehl, H., et al., 1956. Indicator for titration of calcium in presence of magnesium using disodium dihydrogen ethylenediamine tetraacetate. Analytical Chemistry. 28:882–884.

Mohler. 1997. North American Journal of Fisheries Management 17:751–756.

Muncy, R. J., et al. 1990. Inorganic chemical marks induced in fish. Pages 541–546 in N. C. Parker and five coeditors, Fish-marking techniques, American Fisheries Society, Symposium 7, Bethesda, Md.

Oncel, M., et al. 1990. Calcein angiography: a preliminary report on an experimental dye. International Ophthalmology 14: 245–250.

Refojo, M. F., et al. 1972. A new stain for soft hydrophilic lens fitting. Archives of Ophthalmology. 87:275–277.

Wallach, D. F. H., et al. 1959. Preparation and properties of 3,6-dihydroxy-2,4-bis-[N,N'-di(carboxymethyl)-aminomethyl] fluoran. Utilization for the ultramicrodetermination of calcium. Analytical Chemistry 31:456–460.

Wilson, C. A., et al. 1987. Calcein as a fluorescent marker of otoliths of larval and juvenile fish. Transactions of the American Fisheries Society 116:668–670.

What is claimed is:

1. A device for detecting visible fluorescence emitted from a fluorescent-labeled sample comprising:
   (a) a light source which produces incident light;
   (b) a light guide to transmit light from the light source to an excitation filter or bandpass filter;
   (c) a dichroic beamsplitter which reflects all incident light of a predetermined wavelength to a sample;
   (d) a longpass filter or barrier filter through which light from the beamsplitter is transmitted to a line of sight.

2. The device according to claim 1 wherein the light source is selected from the group consisting of mercury vapor lamps, tungsten halogen lamps, xenon lamps, lasers, and combinations thereof.

3. The device according to claim 1 wherein the light guide is a fiber optic light guide.

4. The device according to claim 1 wherein the dichroic beamsplitter and the longpass filter or barrier filter are housed in a single fluor-cluster filter housing positioned at a tip of the light guide.

5. A method of examining a live animal to detect fluorescence comprising:
   contacting said live animal with incident light which has been transmitted through a dichroic beamsplitter which reflects all incident light of a predetermined wavelength to the live animal containing a fluorochrome;
   transmitting light through a barrier filter or longpass filter located in eyeglasses; and
   observing light emitted from the live animal through the barrier filter or longpass filter.

6. The method according to claim 5 wherein the fluorochrome is calcein.

7. The method according to claim 5 wherein the live animal is a salmon.

* * * * *